United States Patent [19]

Oakes et al.

[11] Patent Number: 5,061,485

[45] Date of Patent: Oct. 29, 1991

[54] DISINFECTANT POLYMERIC COATINGS FOR HARD SURFACES

[75] Inventors: Thomas R. Oakes, Stillwater; Daniel E. Pedersen, Cottage Grove; Donna M. Majewski, Lino Lakes, all of Minn.

[73] Assignee: Ecolab Inc., St. Paul, Minn.

[21] Appl. No.: 312,338

[22] Filed: Feb. 16, 1989

Related U.S. Application Data

[63] Continuation of Ser. No. 48,801, May 12, 1987, abandoned.

[51] Int. Cl.$^5$ .............................................. A61K 31/78
[52] U.S. Cl. ......................................... 424/81; 424/78
[58] Field of Search .......................................... 424/81

[56] References Cited

U.S. PATENT DOCUMENTS

| | | | |
|---|---|---|---|
| 2,873,263 | 2/1959 | Lal | 260/45.4 |
| 2,875,097 | 2/1959 | Pritchard | 117/138.5 |
| 3,007,887 | 3/1981 | Essig | 526/212 |
| 3,370,050 | 2/1968 | Seiner | 260/80.81 |
| 3,576,760 | 4/1971 | Gould | 424/28 |
| 3,577,516 | 5/1971 | Gould et al. | 252/403 |
| 3,881,026 | 5/1975 | Shepherd et al. | 426/223 |
| 3,886,125 | 6/1975 | Chromecek | 260/78.3 |
| 3,966,902 | 6/1976 | Chromecek | 424/59 |
| 4,003,991 | 1/1977 | Krohn et al. | 424/81 |
| 4,243,403 | 1/1981 | Jervis et al. | 523/122 |
| 4,374,126 | 2/1983 | Cardarelli et al. | 424/81 |
| 4,483,848 | 11/1984 | Cox et al. | 424/49 |

FOREIGN PATENT DOCUMENTS

56606/86 10/1986 Australia .

OTHER PUBLICATIONS

Evaluation of disinfectants in the domestic invironment under in use conditions by Elizabeth Scott, Sterling Health Research Unit, Sterling Health, Millbank House, Surbiton, Received Jul. 26, 1982, revised Jul. 15, 1983.

An investigation of microbial contamination in the home by Elizabeth Scott, Sally F. Bloomfield, C. G. Barlow accepted Jun. 15, 1982.

Bacterial survey of hygiene in the home follows the Elizabeth Scott, Sally F. Bloomfield and C. G. Barlow.

*Primary Examiner*—Thurman K. Page
*Assistant Examiner*—Peter F. Kulkosky
*Attorney, Agent, or Firm*—Merchant, Gould, Smith, Edell, Welter & Schmidt

[57] ABSTRACT

Liquid disinfectant compositions are disclosed which can be used to surface-coat substrates with polymeric films which are adherent, water-resistant and which can impart prolonged germicidal properties to the treated surfaces.

38 Claims, No Drawings

DISINFECTANT POLYMERIC COATINGS FOR HARD SURFACES

This is a continuation of application Ser. No. 07/048,801, filed May 12, 1987 now abandoned.

FIELD OF THE INVENTION

The invention relates to liquid aqueous compositions that can form adherent, transparent, abrasion resistant polymeric films having prolonged antimicrobial properties. The polymers of the invention are made of a blend of monomers that provide a quality long lasting film that can be easily removed by dilute base.

SUMMARY OF THE INVENTION

Recent studies have indicated that the contamination of both wet and dry household surfaces with potentially pathogenic quantities of bacteria is widespread. Following a study of bacterial flora in 200 homes, Scott et al, in *J. Hy. Camb.*, Vol. 89, 279 (1982) concluded that improved decontamination procedures are necessary, particularly at sites which are repeatedly wetted, such as the surfaces of sinks, toilets, draining boards, stoves, washing machines and the like. However, in controlled in use tests, employing dilute aqueous detergents at kitchen and bathroom sites achieved no observable reduction in microbial contamination, while application of aqueous hypochlorite and phenolic disinfectant compositions only produced a significant reduction in contamination levels for 3–6 hours. In their evaluation of disinfectants in the domestic environment, Scott et al, *J. Hyg. Camb.*, Vol. 92, 193 (1984) hypothesized that the rapid recontamination was due both to re-usage of surfaces such as toilets and to the local multiplication of residual colonies at repeatedly wetted sites such as sinks.

The film forming surface sanitizers introduced to date are prepared in volatile solvents. Such solvents create risks of toxic reaction during use and can be flammable.

Other compositions intended for the controlled release of a disinfectant from a film of a stabilized hydrophilic polymer are disclosed in U.S. Pat. No. 3,966,902. The polymer complex is stabilized as a metal complex by the addition of an inorganic aluminum, zirconium or zinc salt such as aluminum chlorhydrol to the polymerization mixture. The stabilization adjuvant is necessary due to the fact that upon contact with water, films of simple hydrogels become highly swollen and rapidly elute their additives. Furthermore, dry films both simple and metal-complexed hydrogels do not adhere well to ceramic and other hard surfaces and lose their adhesion completely when wetted.

Thus, a need exists for a disinfectant composition capable of forming a polymeric film on hard surfaces such as those formed of ceramics, glass, formica, plastics, metals and the like, which film can entrain a germicidal substance such as a quaternary ammonium salt or a phenolic. A need also exists for a composition capable of yielding a transparent film having strong adhesion to the substrate surface and high resistance against abrasive removal during commonly-employed cleansing procedures. A further need exists for a disinfectant film capable of providing extended protection against microbial contamination. Additionally a need exists for long-lasting films that can be laid down from aqueous solvents but are easily removable under mild basic cleaning conditions.

BRIEF DESCRIPTION OF THE INVENTION

The present invention provides liquid aqueous disinfectant compositions which yield adherent, water-resistant, polymeric films when coated from an aqueous composition onto porous or non-porous hard surfaces and dried. The aqueous liquid compositions comprise germicidal agents which are effective to destroy pre-existing microbial colonies and which impart prolonged antimicrobial properties to the deposited films.

The liquid disinfectant compositions comprise a film-forming copolymer of (a) a monomer having a hydrophilic carboxylic acid ester group, (b) an alpha, beta-unsaturated carboxylic acid ester selected from the group consisting of aromatic esters, cycloalkyl esters and mixtures thereof, and (c) a monomer having a hydrophilic carboxylic acid or carboxylate group. Preferably, the copolymer will comprise about 20 to 99.5 of the hydrophilic carboxylic acid ester monomer, about 0.5 to 80 mol-% of the cycloalkyl or aromatic ester monomer, and about 0.1 to 5 mol-% of the hydrophilic carboxylic acid or carboxylate group containing monomer. The copolymers are substantially free of inorganic metal salt complexation agents such as those disclosed in U.S. Pat. No. 3,966,902. These copolymers can be viewed as modified hydrogels which are surprisingly capable of forming films which are adherent to hard surfaces and are resistant to removal when exposed to water but can easily be removed under conditions of mild base and abrasion.

The films can be readily deposited from neutral or dilute basic solutions or dispersions of the copolymer in a generally aqueous system. Volatile solvent systems are not required for solubility. These liquid systems can also incorporate germicidal agents such as phenols or a quaternary ammonium salt. The agents which are entrapped in the dried polymeric films, and can be incrementally released when the coated surface is contacted with moisture. Contact with atmospheric humidity can assist in maintaining treated surfaces in a substantially microbe-free condition, while exposure to larger amounts of water, as when the surface is moistened by wiping, food residues, dishwater and the like, can lead to the release of increased amounts of the germicide. The polymeric films remain clear and non-tacky, and thus do not detract from the appearance of the surfaces to which they are applied.

Although not wishing to be bound to any theory of action, it is believed that the desirable properties of the present composition are due to (1) the balance of hydrophilic and hydrophobic properties derived from the blend of hydrophilic and hydrophobic monomers, and (2) from the blend of hydrophilic carboxylic acid ester monomer with the hydrophilic acid or acid salt containing monomer to produce aqueous and base solubility, antimicrobial releasability and dilute base solubility of the copolymer. The hydrophilicity of the resultant films may assist both the retention of the germicide and its exposure and activation by externally-applied water. The hydrophobicity imparted to the films by the aromatic and/or the cycloalkyl ester comonomer apparently imparts the necessary adherence and abrasion-resistance to the dried films.

As used herein with respect to antimicrobial action or to the release of a germicide from the present films, the term "prolonged" is intended to refer to the retention of substantial antimicrobial action greater than 4 log reduction preferably greater than 5 log reduction of microbial population as determined by laboratory test methods after 2 aqueous washes and between a 3 log and a 4 log reduction after 2-10 aqueous washes.

As used herein with respect to the solvents used as carriers for the active ingredients of the present compositions, the term aqueous is intended to define solvents or solvent systems which readily evaporate when applied to hard surfaces in thin films at ambient conditions. Such solvents comprise 70 to 99 wt-%, preferably 80 to 90 wt-% water, with the balance comprising water miscible solvents.

As used herein with respect to the surfaces treated by the present compositions, the term "hard" is intended to refer to surfaces composed of refractory materials such as glazed and unglazed tile, brick, porcelain, ceramics, metals, glass and the like, and also includes hard plastics such as formica, polystyrenes, vinyls, acrylics, polyesters, and the like.

Percentages of materials used in the aqueous film-forming composition are weight percentages (wt-%) unless otherwise indicated and the percentages of monomers in the copolymer of the invention is in mol-%.

DETAILED DESCRIPTION OF THE INVENTION

The liquid disinfectant compositions of the present invention comprise an aqueous solution of a minor amount of a film-forming copolymer of (a) a monomer having a hydrophilic carboxylic acid ester functional group, (b) about 0.5 to 80 mol-% of said copolymer of an alpha, beta-unsaturated carboxylic acid ester selected from the group consisting of aromatic esters, cycloalkyl esters, and mixtures thereof, and (c) about 0.1 to 5 mol-% of said copolymer of a hydrophilic monomer having a carboxylic acid or carboxylate functional group. The copolymer is dissolved in a major amount of an aqueous solvent which also incorporates an amount of a germicidal agent effective to impart prolonged antimicrobial properties to the films formed upon removal of the aqueous solvent from coatings of said compositions. Copolymer monomer (b) preferably comprises a mixture of a first monomer comprising a cycloalkyl ester or an aromatic ester of an alpha, beta-unsaturated acid in combination with a second monomer comprising an alkyl ester or an (alkoxy)alkyl ester of an alpha, beta-unsaturated acid wherein the mixture contains about 1 to 90 mol-% of the second monomer based on the first monomer.

The Hydrophilic Monomer

Hydrophilic monomer materials which may be utilized in accord with the present invention are preferably esters of alpha, beta-unsaturated carboxylic acids such as methacrylic acid, acrylic acid, itaconic acid, aconitic acid, cinnamic acid, crotonic acid, mesaconic acid, carboxyethyl acrylic acid, maleic acid, fumaric acid and the like. For example, preferred hydroxyalkyl esters include the esters of these acids and ethylene glycol, di-, tri-, tetra- and (poly)ethylene glycols, propylene glycol and dipropylene glycol; 1,3- or 1,4-butylene glycol; 1,6 hexamethylene glycol, and the like. The preferred unsaturated carboxylic acid portion of the ester monomer includes $C_3$-$C_{10}$-carboxylic acids, i.e., acrylic acid, methacrylic acid, and itaconic acid.

Preferably the film-forming copolymers of the present invention will incorporate about 20-99.5 mol-% of the hydrophilic monomer component, most preferably about 50-95 mol-% based on the polymer.

The Comonomer Modifier

In accord with the present invention, the copolymerization of the hydrophilic monomer with at least one alpha, beta-unsaturated carboxylic acid ester selected from the group consisting of cycloalkyl esters, aromatic esters, and mixtures thereof, substantially improves the adhesion of the copolymer films to hard surfaces. Preferably, the copolymer will include about 0.5-80 mol-% of at least one of these modifying comonomers, most preferably about 1-50 mol-%.

As used herein, the term "cycloalkyl ester" includes bi- and tricycloalkyl esters, and the term "aromatic ester" includes hetero-aromatic esters. Especially preferred cycloalkyl and aromatic esters are those of acrylic acid, methacrylic acid or itaconic acid. Useful aromatic esters of these acids include phenyl, benzyl, tetrahydrofurfuryl, and phenoxyethyl esters. Useful cycloalkyl esters include $C_5$-$C_{12}$ cycloalkyls, e.g. the cyclohexyl, isobornyl and adamantyl esters of these acids.

Alkyl and alkoxy(alkyl) esters of alpha, beta-unsaturated carboxylic acids can be used in combination with the aromatic and/or cycloalkyl ester. Preferably the alkyl esters will be selected from higher (alkyl) esters, such as those of about 5-22 carbon atoms, most preferably about 5-12 carbon atoms. The alkyl and alkoxy (alkyl) esters can be employed to the extent of about 1-90 mol-% by weight of the total of the modifying comonomer. Preferably the mol-% ratio of cycloalkyl or aromatic ester to alkyl ester is about 2:1-1:2.

The alkyl and (alkoxy)alkyl esters of acrylic acid, methacrylic acid and itaconic acid are preferred for use in the present comonomer mixtures.

Examples of these fatty-alkyl ester comonomers which can be employed in combination with cycloalkyl and/or aromatic ester monomers include myristyl, palmityl and stearyl acrylates, methacrylates and itaconates.

Examples of useful $C_5$-$C_{12}$ compounds include hexyl, octyl, ethyl(hexyl), isodecyl and lauryl, acrylates, methacrylates and itaconates. Alkyl esters having branched, as opposed to straight chain moieties are also preferred for use in the present copolymers.

(Alkoxy)alkyl esters useful as comonomers include ($C_1$-$C_4$)alkoxy($C_1$-$C_4$-alkyl) esters of acrylic, methacrylic or itaconic acid such as (methoxy)ethyl, (ethoxy)ethyl, (methoxy)propyl, (ethoxy) propyl and the like.

The Hydrophilic Carboxylic Acid Group Containing Monomer

Suitable hydrophilic monomers containing a carboxylic acid or carboxylate group as a functional group include a vinyl monomer having a free carboxylic acid or carboxylate functional group. The hydrophilic carboxylic acid containing monomer should be polymerizable under the conditions disclosed in the invention and must present free carboxylic acid or carboxylate functional groups to the polymer backbone. We believe it is the carboxylic acid functional groups that provide dilute base and aqueous solubility to the polymer compositions.

Preferred carboxylic acid containing vinyl monomers for use in this invention comprise, for example, 1,4-vinyl benzoic acid, vinyl alcohol esters of dicarboxylic acids, alpha, beta-unsaturated carboxylic acids and dicarboxylic acids, and others.

Most preferred carboxylic acid containing monomers comprise an alpha, beta-unsaturated carboxylic acid including methacrylic acid, acrylic acid, itaconic acid, aconitic acid, cinnamic acid, crotonic acid, mesaconic acid, carboxyethyl acrylic acid, maleic acid, fumaric acid, and the like. Preferably the film forming copolymers of the present invention will incorporate about 0.1 to 5 mol-% of the carboxylic acid or carboxylate containing hydrophilic monomer, most preferably 0.25 to 3 mol-% based on the copolymer.

The Polymerization Reaction

The film-forming copolymers can be prepared by carrying out the polymerization of the mixture of monomer in a solvent or solvent mixture and at concentrations wherein the resultant copolymers remain in solution. Preferred solvents include lower alkanols such as ethanol; ketones, glycol esters or ethers, lower(alkyl)acetates; tetrahydrofuran, dimethylformamide and the like. The monomeric starting materials are typically dissolved in the solvent to the desired concentration, e.g. to a total concentration about 15–30% by weight, although higher or lower concentrations may be employed in some cases.

The polymerization reactions are initiated in the conventional manner and preferably by use of radical-forming initiators. Instances of suitable initiators include dibenzoyl peroxide, tert-butyl peroctoate, cumene hydroperoxide, diazodiisobutyrodinitrile, diisopropylpercarbonate, ammonium persulfate, and the like, per se or in combination with a reducing agent, i.e., in the form of an oxidation-reduction system.

During the course of the reaction,. the reaction mixture may be agitated and heated, preferably in a closed system under an inert atmosphere, to about 50°–100° C., preferably to about 75°–95° C. After completion of the polymerization reaction, a solution of copolymer results, which can be employed without further purification or concentration in the present disinfectant compositions.

The Germicidal Agent

The liquid compositions will incorporate an amount of one or more germicidal agents effective to both disinfect surfaces upon contact and to impart prolonged antimicrobial action to the polymeric films prepared therefrom. A wide variety of antimicrobial agents may be included in effective amounts without inducing undesirable interactions or chemical reactions between the major components of the compositions. Such agents can include chlorhexidine, chlorhexidine gluconate, glutaral, halazone, hexachlorophene, nitrofurazone, nitromersol, povidone-iodine, thimerosol, $C_1$–$C_5$-parabens, hypochlorite salts, clofucarban, clorophen, poloxameriodine, phenolics, mafenide acetate, aminacrine hydrochloride, quaternary ammonium salts, oxychlorosene, metabromsalan, merbromin, dibromsalan, glyceryl laurate, sodium and/or zinc pyrithione, (dodecyl)(diethylenediamine)glycine and/or (dodecyl)(aminopropyl)glycine and the like.

Phenolic compounds are among the preferred germicides for use in the present compositions. Useful phenolic germicides include phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol. The biologically active, water soluble salts of these compounds may also be employed, e.g. the alkali metal salts. Of these compounds o-benzyl-p-chlorophenol is preferred due to its high germicidal power.

Quaternary ammonium salts are also preferred germicides for use in the present invention and include the N-(higher) $C_{10}$–$C_{24}$-alkyl-N-benzyl-quaternary ammonium salts which comprise water solubilizing anions such as halide, e.g., chloride, bromide and iodide; sulfate, methosulfate and the like and the heterocyclic imides such as the imidazolinium salts.

For convenience, the aliphatic quaternary ammonium slats may be structurally defined as follows:

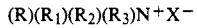

$$(R)(R_1)(R_2)(R_3)N^+X^-$$

wherein R is benzyl, or lower(alkyl) benzyl; $R_1$ is alkyl of 10 to 24, preferably 12 to 22 carbon atoms; $R_2$ is $C_{10}$–$C_{24}$-alkyl, $C_1$–$C_4$-alkyl or $C_1$–$C_4$-hydroxyalkyl, $R_3$ is lower alkyl or hydroxyalkyl of 1 to 4 carbon atoms and X represents an anion capable of imparting water solubility or dispersibility including the aforementioned chloride, bromide, iodide, sulfate and methosulfate. Particularly preferred species of these aliphatic quats include N-$C_{12}$–$C_{18}$-alkyldimethylbenzylammonium chloride (myrisalkonium chloride), n-$C_{12}$–$C_{24}$-alkyldimethyl (ethylbenzyl) ammonium chloride (quaternium 14), dimethyl(benzyl)ammonium chloride and mixtures thereof. These compounds are commercially available as the BTC series from Onyx Chemical Co., Jersey City, N.J. For example, BTC 2125M is a mixture of myrisalkonium chloride and quaternium-14.

Other useful aliphatic quaternary ammonium compounds include the N,N-di-(higher)-$C_{10}$–$C_{24}$-alkyl-N,N-di(lower)-$C_1$–$C_4$-alkyl-quaternary ammonium salts such as distearyl(dimethyl)ammonium chloride, cetyl(dimethyl)ethyl ammonium bromide, dicoco(dimethyl)ammonium chloride, dihydrogenated tallow(dimethyl)ammonium chloride, di-tallow(dimethyl)ammonium chloride, distearyl(dimethyl)ammonium methosulfate cetyl(trimethyl)ammonium bromide and dihydrogenated-tallow(dimethyl)ammonium methosulfates.

Other useful nitrogenous germicides include benzethonium chloride, cetylpyridinium chloride, methylbenzethonium chloride, domiphen bromide, gentian violet, and the like.

The total concentration of the germicidal component of the present liquid compositions can vary widely, depending upon its antimicrobial activity, solubility, stability and the like. The present disinfectant compositions will preferably comprise about 0.01–10%, most preferably about 0.05–5% by weight of the phenolic or quaternary ammonium salts based on the disinfectant polymeric composition as a whole. Highly durable, abrasion resistant films can be achieved when the total concentration of the germicidal agent in the present compositions comprises about 0.01–50%, preferably about 0.25–20%, and most preferably about 0.5–15% by weight based on the weight of the dissolved copolymers.

Preparation and Application of the Compositions

The present film-forming liquid compositions are readily prepared by dissolving the germicidal agent in an aqueous solution of the copolymer with agitation under ambient conditions, followed by dilution of the resultant solution to the appropriate concentration by addition of water or other predominately aqueous solvent system. Since the copolymer is commonly prepared in a volatile solvent such as a lower(alkanol) or a lower(alkyl)acetate, this solution can be diluted with a water to reach at least 70 wt-% preferably greater than 75 wt-% water. Alternatively, the volatile solvent containing polymer product can be removed using heat and/or vacuum to produce the neat polymer. The neat polymer can then be taken up into a water solution using 0.01–1.0N base as an aid for solubility. Therefore, the preferred liquid disinfectant compositions of the present invention will comprise about 0.25–10%, preferably about 0.5–5% of the film-forming copolymer; about 0.10–10%, preferably about 0.5–5% of the germicidal agent, most preferably selected from a phenolic or quaternary ammonium salt; the remainder of the composition being the aqueous solvent-system.

Preferably the film-forming copolymer will incorporate about 50–95- mol-% of the hydrophilic monomer, most preferably 2-hydroxyethylmethacrylate or 2-hydroxyethylacrylate; about 10–35 mol-% of a $C_5$–$C_8$-cycloalkyl acrylate or methacrylate, an aromatic acrylate or methacrylate or mixtures thereof, and about 0.1 to 5 mol-% of a hydrophilic carboxylic acid or carboxylate monomer containing monomer. Preferably the carboxylic acid or carboxylate monomer comprises acrylic acid, methacrylic acid or mixtures thereof. Optionally, a higher(alkyl)acrylate or methacrylate monomer will also be included in the copolymer, replacing the cycloalkyl and/or aromatic monomer to the extent of about 25–75 mol-%. Minor amounts of adjuvants such as an indicator of germicide level, fragrance, surfactants, dyes and the like may also be included in the present compositions, insofar as they are compatible with the film-forming process. For example, about 0.5–5% of a compatible surfactant can be included in the present compositions to enhance their cleaning power.

The finished disinfectant compositions are homogenous liquids which are applied to the surfaces to be treated by dipping, spraying, brushing, roller coating, pad coating or using similar coating procedures. For household applications, hand-operated pump-type or pressurized aerosol sprayers can be effective. Although the present compositions are particularly adapted to adhere to hard surfaces, they can also be employed to coat or otherwise treat materials such as sponges, flexible plastics, textiles, wood and the like. Generally, the coating process is continued to the extent required to deliver an amount of the liquid composition which rapidly dries to a clear, uniform polymeric film under ambient conditions, e.g., about 50–100 mg/in$^2$ of liquid composition is generally effective to disinfect and impart prolonged antimicrobial protection to tile surfaces. The germicidal films are glossy, resistant to mild abrasion and are not broken or substantially depleted of biocide by slow release caused by repeated wettings. Repeated application of the liquid compositions does not result in substantial film build-up since the reapplication can act to resolubilize and level the prior-applied film, the film can easily be removed with dilute acid base. The invention will be further described by reference to the following detailed Examples.

COMPARATIVE EXAMPLE A

Copolymer Preparation

Cyclohexylmethacrylate, 5 mol-% (2.46 g), isodecyl methacrylate, 5 mol-% (3.31 g) and 2-hydroxyethyl methacrylate 90 mol-% (34.23 g) were dissolved in 160 ml of ethyl alcohol and 0.4 g of dibenzoyl peroxide were added. The solution was bubbled with nitrogen for 10 minutes and heated in a closed system (pressure bottle) for 8 hours at 80° C. The resulting solution of the copolymer was used for the preparation of disinfectant compositions.

COMPARATIVE EXAMPLE B

Comparison Copolymer Preparation

A copolymer solution was prepared by the procedure of Example A, with the exception that 7.0 mol-% cyclohexyl methacrylate, 3.0 mol-% isodecyl methacrylate and 90 mol-% 2-hydroxyethylmethacrylate were copolymerized.

COMPARATIVE EXAMPLE C

Comparison Copolymer Preparation

A copolymer solution was prepared by the procedure of Example A, except that 3.0 mol-% cyclohexyl methacrylate, 7 mol-% isodecyl methacrylate and 90 mol-% 2-hydroxyethyl methacrylate were employed.

COMPARATIVE EXAMPLE D

A copolymer solution was prepared by the procedure of Example A with the exception that 10 mol-% of cyclohexyl methacrylate was used with no isodecyl methacrylate.

Evaluation of Copolymer Comparative Preparation

The ethanolic polymer solutions were slowly diluted with an equal volume of deionized water. As the addition of the water to the ethanolic polymer solutions began, the solution immediately became cloudy and as the proportion of water increased the water insoluble polymer formed a white gummy dispersion/precipitate in the water solution. On standing, the water insoluble polymer coated the container with a white gummy, oily, polymeric film. The polymers free of the carboxylic acid containing monomer composition were insufficiently water soluble to form an aqueous solution that could be used to deposit the polymeric film onto a surface requiring sanitization.

EXAMPLES 1–12

Following the general polymerization procedure set forth in Comparative Example A, the polymer preparations shown in the Tables following describe the preparation of polymers containing carboxylic acid groups that render the polymer composition water soluble for use in aqueous systems.

TABLE I

Surface Sanitizer-New Polymers

| Composition (Mol-%) | Example 1 | 2 | 3 | 4 |
|---|---|---|---|---|
| HEMA | 89.5 | 89 | 88.5 | 88.5 |
| Cyclo-Hex MA* | 3 | 3 | 3 | 10 |
| Iso-Decyl MA | 7 | 7 | 7 | — |
| Methacrylic acid | 0.5 | 1.0 | 1.5 | 1.5 |
| Before Washing: | | | | |
| Clear/Haze | C | C | C | C |
| Smooth/Rough | S | S | S | S |
| Uniformity (Good/Poor) | G | G | G | G |
| After 20 Washes, TRITON | | | | |

TABLE I-continued

| Surface Sanitizer-New Polymers | | | | |
|---|---|---|---|---|
| | Example | | | |
| Composition (Mol-%) | 1 | 2 | 3 | 4 |
| X-100 Film Applied: | | | | |
| Excellent/Good/Fair/Poor | E | E | E | Very slight haze |
| Film Wear: | | | | |
| % Film Removed | 8 | 10 | 10 | 15 |
| Peeling | — | — | Very slight | Very slight |
| Formula tested: | | | | |
| Polymer | 15% | | | |
| BTC 2125M (80%)** | 0.625% | | | |
| Ethanol | 84.375% | | | |

*MA = methacrylate
**n-alkyl (mixture of a 60% $C_{14}$, 30% $C_{14}$, 5% $C_{12}$ and 5% $C_{18}$ with a 68% $C_{12}$ and 32% $C_{14}$ Quat) dimethyl benzyl ammonium chloride The data relating to the quality and durability of the films was obtained by casting an ethanolic solution of the polymers on a tile surface. The following Tables show the quality of the film cast from aqueous solution.

TABLE II

| Surface Sanitizer-New Polymers Water Based Formulas | | |
|---|---|---|
| | Example | |
| Composition (Mol-%) | 5 | 6 |
| HEMA + 0.1% methacrylic acid | — | 90 |
| HEMA + 1.5% methacrylic acid | 90 | — |
| Cyclo-Hex MA* | 3 | 3 |
| Iso-Decyl MA | 7 | 7 |
| AIBN | 0.25 | 0.25 |
| Acetic acid | 0.10 | — |
| Before Washing: | | |
| Clear/Haze | C | C |
| Smooth/Rough | S | S |
| Uniformity (Good/Poor) | G | G |
| After # Washes, | 20 | 2 |
| TRITON X-100 Film Applied: | | |
| Film Wear: | | |
| Excellent/Good/Fair/Poor | VG | P |
| % Film Removed | 5 | 95 |
| Formula tested: | | |
| Polymer | 20.0 | 20.0 |
| Acetic acid | 0.10 | — |
| Q-372** | 1.32 | 1.32 |
| Distilled water | 78.58 | 78.68 |

*MA = methacrylate
**n-alkyl dimethyl benzyl ammonium chloride (alkyl group in 40% $C_{12}$, 50% $C_{14}$ and 10% $C_{16}$

EXAMPLE 7-12

The following Table IV displays aqueous preparations made by combining the ethanolic solution of polymer prepared in Examples 7, 8 9, 10, 11 and 12 with water, $NH_4OH$ and a quaternary ammonium salt sanitizing agent in the wt-% proportions displayed in the Table.

TABLE III

| | Formula Stability and Film Appearance | | | | | |
|---|---|---|---|---|---|---|
| | 7 | 8 | 9 | 10 | 11 | 12 |
| Ex. 6 | 28.8 | — | — | — | — | — |
| Ex. 6 | — | 28.8 | — | — | — | — |
| Ex. 5 | — | — | 15.00 | — | — | — |
| Ex. 5 | — | — | — | 15.00 | — | — |
| Ex. 6 | — | — | — | — | 15.00 | — |
| Ex. 5 | — | — | — | — | — | 20.00 |
| $NH_4OH$ | 0.50 | 1.00 | 0.26 | 0.26 | 0.26 | 0.34 |

TABLE III-continued

| | Formula Stability and Film Appearance | | | | | |
|---|---|---|---|---|---|---|
| | 7 | 8 | 9 | 10 | 11 | 12 |
| Quat D. | 1.50 | 1.50 | 0.95 | 0.95 | 0.95 | 1.30 |
| water | 68.50 | 68.50 | 83.80 | 83.80 | 83.80 | 71.06 |
| propylene glycol | — | — | — | — | — | 0.3 |

The aqueous preparations displayed in the table were clear and stable.

The following Table shows that the formulations can achieve a 5 log reduction in microbial populations for at least four washes after application and can achieve between a 3 and 4 log reduction in microbial population through 10 washes of the film with no additional film application.

TABLE IV

| Sanitizing Capacity Average Log Reduction in Microbial Population | | | | | |
|---|---|---|---|---|---|
| Formulation | 0 | 2 | 4 | 6 | 10 |
| 7 | 6.0 | 5.8 | 5.8 | 6.3 | 4.4 |
| 8 | 5.9 | >6.2 | 5.5 | 5.1 | 3.2 |
| 9 | 6.7 | 5.8 | 5.5 | 4.8 | 3.2 |
| 10 | 5.7 | 4.4 | 6.7 | 6.5 | 6.9 |
| 11 | 5.0 | 5.8 | 5.2 | 5.3 | 3.4 |
| 12 | 6.2 | 6.1 | 6.0 | 5.3 | 5.0 |
| S.S. Control | 6.3 | 5.9 | 6.1 | 6.6 | 4.1 |

The above data, showing effective sanitization of surfaces using the composition of the inventor, were developed using the following procedure:

This test is designed to determine the ability of a surface sanitizer formulation to give reduction of transient microbial contamination when used in sanitizing precleaned nonporous food contact and/or non-food contact surfaces. It is also intended to determine the formulations ability to leave a residual antimicrobial film.

1. REAGENTS a) Culture Media-Cultures are maintained following AOAC Methods, as specified in Sections 4.001–4.002 and 4.020 of the Official Methods of Analysis of AOAC, 14th Edition (1984).

Cultures are maintained on nutrient agar slants by monthly transfers, except Ps. aeruginosa which is carried on Cystine Trypticase agar, as specified in Section 4.001.

From the above stock cultures, tubes of AO AC nutrient broth are inoculated and incubated at 37° C.+1° C. Broth cultures are transferred daily with incubation at 37° C. Cultures used for these tests are incubated 18-24 hours at 37° C.

b) Subculture Media.- Use Tryptone Glucose Extract Agar.

c) Neutralizer blanks.-Prepare as described in AOAC Methods 4.020 (c), (d), or other appropriate neutralizer material should be employed.

d) Phosphate buffer dilution blanks.- Prepared as described in AO AC Methods 4.020 (e), (f).

(e) Test Organisms.

For a non-food contact hard surface sanitizer claim, product must be tested against *Stapylococcus aureus* (ATCC 6538) and *Klebsiella pneumonia*, aberrant, (ATCC 4352). *Enterobacter aerogenes* (ATCC 13048) may be substituted for *K. pneumoniae*. For a food contact hard surface sanitizer claim, product must be tested against *Staphylococcus aureus* (ATCC 6538) and *Escherichia coli* (ATCC 11229).

2. RESISTANCE OF PHENOL TO TEST CULTURES

Determine resistance to phenol at least every 3 months by AOAC Method 4.001–4.005.

3. APPARATUS a) Glassware—Sterile Bactereiological Pipettes. Sterilize at 180° F. in hot air oven—2 hours.
b) Petri Dishes—Sterile—100×15 mm.
c) Cotton Swatches—Sterile—1"×1".
d) Forceps—Sterile.

4. PREPARATION OF CULTURE SUSPENSION:

From stock cultures inoculate tube of AOAC nutrient broth, AOAC 4.001 A, and make - 3 consecutive daily transfers (−30), incubating transfers 20–24 hours at 37° C.+1. Do not use transfer >30 days. If only 1 daily transfer has been missed, no special procedures are required; if 2 daily transfers are missed, repeat with 3 daily transfers.

5 PREPARATION OF TEST SURFACES

Test surfaces may include, but are not limited to, the following glazed and unglazed ceramic, glass, PVC plastic, Formica, and stainless steel.

Test surfaces are precleaned 4" by 4" square tiles that are wiped with Isopropyl Alcohol just prior to applying the product to the surface. Product formulations are applied evenly to the entire square surface as per instructions. Tiles are allowed to air dry at room temperature.

Control surfaces containing all ingredients except the antimicrobials are also prepared as above, along with a control surface which has no surface treatment.

6. OPERATING TECHNIQUE a. Treated surfaces, prepared as above, are inoculated with 1.0 ml of the organism being tested. Inoculum is prepared by adding 11 ml of an 18–24 hour culture, prepared as described in Step 1(a), to 99 ml of sterile buffered water and mixed well.

b. Inoculum is spread evenly over the entire surface using a sterile glass spreader.

c. Inoculated tiles are allowed to air dry 30 minutes at 37° C.

d. Initial inoculum is plated using Tryptone Glucose Extract Agar to verify a viable culture and to enumerate the surface inoculum level.

e. Surviving microorganisms are then recovered by swabbing the entire tile surface with a sterile 1" square cotton swatch which has been wetted with sterile buffered water, approximately 0.5 ml. Cotton swatches are handled aseptically using flamed forceps.

f. Swabbing of the surface is accomplished by wiping the cloth across the surface using a back and forth motion four times.

g. Transfer swatch immediately to a sterile tube containing 9.0 ml of appropriate neutralizing broth.

h. Vortex tubes for approximately 15 seconds and immediately prior to plating for another 5 seconds.

i. Plate samples, using serial 10-fold dilutions. to enumerate surviving organisms. Use Tryptone Glucose Extract Agar.

j. Incubate plates at 37° C. for 48 hours and enumerate.

ALTERNATE PROCEDURE a. Treated surfaces, prepared as above, are inoculated with 1.0 ml of the organism being tested. Inoculum is prepared by adding 11 ml of an 18–24 hour culture, prepared as described in Step 1(a), to 99 ml of sterile buffered water and mixed well.

b. Inoculum is spread evenly over the entire surface using a sterile glass spreader.

c. Inoculated tiles are allowed to air dry 30 minutes at 37° C.

d. Initial inoculum is plated using Tryptone Glucose Extract Agar to verify a viable culture and to enumerate the surface inoculum level.

e. Surviving microorganisms are then recovered by swabbing the entire tile surface with a sterile 1" square cotton swatch which has been wetted with sterile buffered water, approximately 0.5 ml. Cotton swatches are handled aseptically using flamed forceps.

f. Swabbing of the surface is accomplished by wiping the cloth across the surface using a back and forth motion four times.

g. Transfer swatch immediately to a sterile tube containing 9.0 ml of appropriate neutralizing broth.

h. Vortex tubes for approximately 15 seconds and immediately prior to plating for another 5 seconds.

i. Plate samples, using serial 10-fold dilutions to enumerate surviving organisms. Use Tryptone Glucose Extract Agar.

j. Incubate plates at 37° C. for 48 hours and enumerate.

k. Wash tiles using a 4"×4" Kay Dry towel which has been thoroughly wetted using 15.0 ml of the respective wash solution, either distilled/deionized water or a 0.15% solution of Triton X-100 w/v in deionized water.

l. Wash surfaces using approximately 1–2 lbs. of pressure in a back and forth motion twice covering the whole tile.

m. Blot surface dry using a Kim Wipe.

n. Inoclulate tiles, recover surviving organisms, and plate following above procedures a–j.

o. Repeat Steps k–n until the surface treatments prove to be ineffective in reducing bacterial contamination when compared to the proper control or until the product survives the number of washes necessary to meet product claims.

7. RESULTS

To be considered valid, results must meet standard effectiveness:

For a hard surface sanitizer claim for food contact surfaces, a 99.999% reduction in count of number of organisms when compared to the proper control numbers, is required.

For a hard surface sanitizer claim for non-food contact surfaces, a 99.9% reduction in count of number of organisms when compared to the proper control numbers, is required.

STERILITY CONTROLS a) Neutralizer—Plate 1 ml from previously unopened tube.
b) Water—Plate 1 ml from each type of water used.
c) Media—Pour one plate from previously unopened bottle.

The above discussion examples and data provide a thorough understanding of the invention. However, since many embodiments of the sanitizer compositions of the invention can be made without departing from the spirit and scope of the invention, the invention resides in the claims hereinafter appended.

We claim:

1. A liquid antimicrobial film-forming composition free of complexed inorganic metal salt wherein said composition comprises copolymers adherent to hard surfaces upon film formation, said film being abrasion resistant and soluble in dilute base, said composition comprising a homogenous solution in an aqueous solvent of (i) an amount of germicidal agent effective to impart prolonged renewable antimicrobial properties and (ii) a film-forming water soluble copolymer, said copolymer consisting essentially of:
   (a) about 20-99.5 mol-% of said copolymer of a hydroxy alkyl carboxylic acid ester monomer;
   (b) about 0.5-50 mol-% of said copolymer of a monomer selected from the group consisting of an aromatic ester, a cycloalkyl ester, an ester mixture thereof of an alpha, beta-unsaturated carboxylic acid; and
   (c) about 0.1 to 5 mol-% of said copolymer of a monomer having a hydrophilic carboxylic acid or carboxylate functional group.

2. The composition of claim 1 wherein, in component (c), the hydrophilic carboxylic acid or carboxylate functional group containing monomer comprises an alpha, beta-unsaturated carboxylic acid or salt thereof.

3. The composition of claim 2 wherein the alpha, beta-unsaturated carboxylic acid comprises acrylic acid or methacrylic acid.

4. The composition of claim 1 wherein component (b) comprises a cycloalkyl or an aromatic ester of an alpha, beta-unsaturated carboxylic acid ester monomer in combination with about 1-90 mol-% of an alkyl or alkoxy alkyl ester of an alpha, beta-unsaturated acid based on the component (b).

5. The composition of claim 4 wherein the alkyl ester is a $C_{5-22}$ alkyl ester and the alkoxy alkyl ester is a $C_{1-4}$ alkoxy $C_{1-4}$ alkyl ester.

6. The composition of claim 1 wherein the copolymer comprises about 50-99.5 mol-% of the monomer of component (a).

7. The composition of claim 6 wherein the monomer of component (a) comprises a hydroxyalkyl ester of an alpha, beta-unsaturated carboxylic acid.

8. The composition of claim 7 wherein, in component (a), the hydroxyalkyl ester comprises a hydroxyalkyl acrylate or hydroxyalkyl methacrylate.

9. The composition of claim 7 wherein, in component (a), the alpha, beta-unsaturated carboxylic acid comprises acrylic acid, methacrylic acid, itaconic acid or mixtures thereof.

10. The composition of claim 1 wherein the copolymer comprises about 0.25-15 wt-% of the antimicrobial film-forming liquid composition.

11. The composition of claim 1 wherein the germicidal agent comprises a quaternary ammonium salt, and the aqueous solvent comprises greater than about 55 wt-% water.

12. The composition of claim 11 wherein the composition comprises about 0.01-10 wt-% of the quaternary ammonium salt.

13. The composition of claim 1 wherein the germicidal agent comprises about 0.01-50 wt-% of the copolymer and the aqueous solvent comprises greater than 55 wt-% water.

14. The composition of claim 1 wherein the solvent comprises a mixture of water and about 0.1 to 35 wt-% of a $C_{1-4}$ alkanol.

15. A liquid disinfectant antimicrobial film-forming composition free of a complexed inorganic metal salt wherein said composition comprises copolymers adherent to hard surfaces upon film formation, said film being abrasion resistant and soluble in dilute base, said composition consisting essentially of a homogenous solution, in an aqueous solvent, of an amount of a germicidal agent effective to impart prolonged renewable disinfectant, antimicrobial properties and a film-forming water soluble polymer, said polymer consisting essentially of:
   (a) about 50-95 mol-% of a hydrophilic monomer selected from the group consisting of a 2-hydroxyethyl methacrylate, 2-hydroxypropyl methacrylate, and 3-hydroxypropyl methacrylate;
   (b) about 1-10 mol-% of said copolymer of an aromatic or cycloalkyl ester of an alpha, beta-unsaturated acid; and
   (c) about 0.1 to 5 mol-% of said copolymer of a hydrophilic carboxylic acid or carboxylate containing monomer selected from the group consisting of acrylic acid, methacrylic acid and maleic anhydride.

16. The composition of claim 15 wherein the film-forming copolymer is present at a concentration of about 0.5-5% of the liquid film-forming antimicrobial composition.

17. The composition of claim 15 wherein the Alpha, Beta unsaturated acid is methacrylic acid, acrylic acid or itaconic acid.

18. The composition of claim 15 wherein the aromatic ester is a phenyl, benzyl or tetrahydrofurfuryl ester.

19. The composition of claim 15 wherein the cycloalkyl ester is a cyclohexyl, isobornyl or adamantyl ester.

20. The composition of claim 15 wherein the germicidal agent is present at a concentration of about 0.05-5% of the composition and is a germicidal quaternary ammonium salt.

21. The composition of claim 20 wherein the quaternary ammonium salt is a $C_{10}$-$C_{20}$-n-alkyl (dimethyl)benzyl ammonium salt.

22. The composition of claim 15 wherein the germicidal agent comprises about 0.25-20% by weight of the germicidal agent.

23. The composition of claim 15 wherein the aqueous solvent is a water-alcohol mixture having more than 55 wt-% water.

24. The composition of claim 1 wherein the aqueous solvent comprises a mixture of water and a lower(alkanol) at a concentration in the solvent of less than about 20%.

25. The composition of claim 24 wherein at least about 85% by weight of the composition comprises the aqueous solvent.

26. A method for disinfecting and imparting prolonged germicidal properties to a hard porous or nonporous surface comprising coating said surface with the composition of claims 1 or 13, and removing the aqueous solvent from said coating to form a germicidal, water-resistant polymeric film thereupon.

27. The method of claim 26 wherein about 10-100 mg of the composition is applied per square inch of surface.

28. The liquid antimicrobial film-forming composition of claim 1 wherein the germicidal agent comprises a phenolic compound.

29. The liquid antimicrobial film-forming composition of claim 28 wherein the phenolic compound comprises a biologically active, water soluble salt of a phenolic compound selected from the group consisting of phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol, or combinations thereof.

30. A liquid antimicrobial film-forming composition of claim 1 wherein said germicidal agent comprises o-benzyl-p-chlorophenol.

31. The liquid antimicrobial film-forming composition of claim 15 wherein the germicidal agent comprises a phenolic compound.

32. The liquid antimicrobial film-forming composition of claim 31 wherein the phenolic compound comprises a biologically active, water soluble salt of a phenolic compound selected from the group consisting of phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butylphenol and o-benzyl-p-chlorophenol, or combinations thereof.

33. A liquid antimicrobial film-forming composition of claim 15 wherein said germicidal agent comprises o-benzyl-p-chlorophenol.

34. A liquid antimicrobial film-forming composition free of complexed inorganic metal salt wherein said composition comprises copolymers adherent to hard surfaces upon film formation, said film being abrasion resistant and soluble in dilute base, said composition comprising a homogenous solution in an aqueous solvent of (i) an amount of germicidal agent effective to impart prolonged renewable antimicrobial properties and (ii) a film-forming water soluble copolymer, said copolymer consisting essentially of:
  (a) about 88.5–89.5 mol-% of said copolymer of a hydroxy alkyl carboxylic acid ester monomer;
  (b) about 3–10 mol-% of said copolymer of a monomer selected from the group consisting of an aromatic ester, a cycloalkyl ester, an ester mixture thereof of an alpha, beta-unsaturated carboxylic acid; and
  (c) about 0.5–1.5 mol-% of said copolymer of a monomer having a hydrophilic carboxylic acid or carboxylate functional group; and
  (d) about 0–7 mol-% of said copolymer of a monomer consisting of an aliphatic ester of an alpha, beta-unsaturated carboxylic acid.

35. The composition of claim 34 wherein said hydroxy alkyl carboxylic acid ester monomer comprises hydroxy ethyl methacrylate.

36. The composition of claim 34 wherein said cycloalkyl ester of an alpha, beta-unsaturated carboxylic acid comprises cyclohexyl methacrylate.

37. The composition of claim 34 wherein said aliphatic ester of an alpha, beta-unsaturated carboxylic acid comprises isodecyl methacrylate.

38. The composition of claim 34 wherein said hydrophilic carboxylic acid or carboxylate functional group containing monomer comprises methacrylic acid.

* * * * *

UNITED STATES PATENT AND TRADEMARK OFFICE
CERTIFICATE OF CORRECTION

PATENT NO. : 5,061,485

DATED : October 29, 1991

INVENTOR(S) : Thomas R. Oakes, Daniel E. Pedersen, and Donna M. Majewski

It is certified that error appears in the above-identified patent and that said Letters Patent is hereby corrected as shown below:

In Column 7, line 57, after the word "dilute", delete the word "acid".

In Column 7, line 68, after the word "of", insert --95%--.

In Column 14, line 54, "1" should read --15--.

In Column 15, line 8, "phenyl" should read --phenol--.

Signed and Sealed this

Twenty-seventh Day of April, 1993

Attest:

MICHAEL K. KIRK

*Attesting Officer*     *Acting Commissioner of Patents and Trademarks*